(12) United States Patent
Tashiro

(10) Patent No.: US 10,206,660 B2
(45) Date of Patent: *Feb. 19, 2019

(54) ULTRASOUND DIAGNOSTIC METHOD DISPLAYING BODY MARKS EACH OF WHICH INDICATES AN EXAMINATION POSITION BY THE ULTRASOUND PROBE

(71) Applicant: FUJIFILM Corporation, Tokyo (JP)

(72) Inventor: Rika Tashiro, Tokyo (JP)

(73) Assignee: FUJIFILM CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/037,037

(22) Filed: Jul. 17, 2018

(65) Prior Publication Data

US 2018/0317885 A1 Nov. 8, 2018

Related U.S. Application Data

(63) Continuation of application No. 14/034,809, filed on Sep. 24, 2013, now Pat. No. 10,070,845.

(30) Foreign Application Priority Data

Sep. 25, 2012 (JP) ................. 2012-210590

(51) Int. Cl.
*A61B 8/00* (2006.01)
*A61B 8/08* (2006.01)

(52) U.S. Cl.
CPC ............... *A61B 8/463* (2013.01); *A61B 8/08* (2013.01); *A61B 8/465* (2013.01); *A61B 8/469* (2013.01);

(Continued)

(58) Field of Classification Search
CPC combination set(s) only.
See application file for complete search history.

(56) References Cited

U.S. PATENT DOCUMENTS 5,161,535 A 11/1992 Short et al.
5,315,999 A 5/1994 Kinicki et al.
(Continued)

FOREIGN PATENT DOCUMENTS

JP 6-65338 B2 8/1994
JP 2001-137237 A 5/2001
(Continued)

OTHER PUBLICATIONS

United States Notice of Allowance dated May 16, 2018 in U.S. Appl. No. 14/034,809.
(Continued)

*Primary Examiner* — Serkan Akar
*Assistant Examiner* — Farshad Negarestan
(74) *Attorney, Agent, or Firm* — McGinn I.P. Law Group, PLLC

(57) ABSTRACT

An ultrasound diagnostic method utilizing an ultrasound diagnostic apparatus including an ultrasound probe, including controlling operations of the ultrasound diagnostic apparatus on the basis of an instruction signal input from an operator and displaying, in response to an operation by the operator, a plurality of first body marks on a first display screen at a time, each of the first body marks being different from each other in a body pattern which is a patterning of a body part seen in a predetermined direction, and being further superimposed on by a probe mark which indicates a position and a direction on the body pattern which the ultrasound probe is put.

13 Claims, 8 Drawing Sheets

(52) U.S. Cl.
CPC .............. *A61B 8/54* (2013.01); *A61B 8/4427* (2013.01); *A61B 8/462* (2013.01); *A61B 8/585* (2013.01)

(56) References Cited

U.S. PATENT DOCUMENTS

| | | |
|---|---|---|
| 6,458,081 B1 | 10/2002 | Matsui et al. |
| 2002/0028996 A1 | 3/2002 | Uehara |
| 2003/0135116 A1 | 7/2003 | Ogasawara et al. |
| 2004/0179332 A1 | 9/2004 | Smith et al. |
| 2006/0270938 A1 | 11/2006 | Yawata |
| 2007/0299342 A1 | 12/2007 | Hayasaka |
| 2008/0267499 A1 | 10/2008 | Seischinger et al. |
| 2010/0094100 A1 | 4/2010 | Fujii et al. |
| 2010/0305444 A1 | 12/2010 | Fujii et al. |
| 2010/0312113 A1 | 12/2010 | Ogasawara et al. |
| 2011/0178405 A1 | 7/2011 | Chono |
| 2011/0263980 A1 | 10/2011 | Mills et al. |
| 2012/0014578 A1 | 1/2012 | Karssemeijer et al. |
| 2012/0262460 A1 | 10/2012 | Endo et al. |
| 2013/0261447 A1 | 10/2013 | Tashiro |
| 2014/0309530 A1 | 10/2014 | Chono |
| 2015/0057541 A1 | 2/2015 | Yang et al. |

FOREIGN PATENT DOCUMENTS

| | | |
|---|---|---|
| JP | 2003-153903 A | 5/2003 |
| JP | 2006-271862 A | 10/2006 |
| JP | 2006-333896 A | 12/2006 |
| JP | 2007-020456 A | 2/2007 |
| JP | 2010-115478 A | 5/2010 |
| JP | 2011-030583 A | 2/2011 |
| WO | WO 2011/065392 A1 | 6/2011 |
| WO | WO 2012/161040 A1 | 11/2012 |

OTHER PUBLICATIONS

United States Office Action dated Feb. 28, 2017 in U.S. Appl. No. 14/034,809.
United States Office Action dated Aug. 9, 2016 in U.S. Appl. No. 14/034,809.
United States Office Action dated Jan. 22, 2016 in U.S. Appl. No. 14/034,809.
United States Office Action dated Jul. 7, 2015 in U.S. Appl. No. 14/034,809.
Chinese Office Action dated Jul. 15, 2016 with an English translation thereof.
Japanese Office Action dated Sep. 1, 2015 with a partial English translation.
Japanese Office Action dated Nov. 4, 2015 with a partial English translation.
Japanese Office Action dated Aug. 25, 2015 with a partial English translation.
United States Office Action dated Apr. 19, 2016 in U.S. Appl. No. 14/958,204.
United States Office Action dated Jun. 3, 2015 in co-pending U.S. Appl. No. 13/846,719.

ULTRASOUND DIAGNOSTIC METHOD DISPLAYING BODY MARKS EACH OF WHICH INDICATES AN EXAMINATION POSITION BY THE ULTRASOUND PROBE

CROSS-REFERENCE TO RELATED APPLICATIONS

The present application is a Continuation Application of U.S. patent application Ser. No. 14/034,809, filed on Sep. 24, 2013, which is based on Japanese Patent Application No. 2012-210590 filed on Sep. 25, 2012, the entire contents of which are hereby incorporated by reference.

BACKGROUND OF THE INVENTION

The present invention relates to an ultrasound diagnostic apparatus and in particular, to an ultrasound diagnostic apparatus to generate an ultrasound image based on reception signal obtained by transmission and reception of the ultrasonic waves using an ultrasound probe and to display the ultrasound image on a display unit.

In the medical field, an ultrasound diagnostic apparatus using an ultrasound image has been put into practical use. Generally, in this kind of ultrasound diagnostic apparatus, the ultrasound image is generated by transmitting an ultrasonic wave toward a subject from a transducer array of an ultrasound probe, receiving an ultrasonic echo from the subject by the transducer array, and processing the reception signal electrically in a diagnostic apparatus body.

In recent years, an ultrasound diagnostic apparatus has been developed in which various examinations are performed on the basis of ultrasound images and an assist of examinations themselves is also performed so that an operator who has little experience or knowledge can perform examinations. For example, JP 6-65338 B describes that diagnostic portion specifying patterns comprising diagnostic portions and marks of probe positions corresponding to the diagnostic portions are arranged in the vicinity of an operation selecting unit in the order corresponding to diagnoses. Further, JP 2010-115478 A and JP 2011-30583 A disclose an ultrasound diagnostic apparatus in which an examination procedure (operation procedure) is registered in advance and examinations may be performed according to the registered examination procedure.

According to such ultrasound diagnostic apparatuses as described above, it is possible to perform an operation easily and to perform examinations efficiently.

SUMMARY OF THE INVENTION

However, in ultrasound diagnosis, since in many cases, a series of examinations are performed while sequentially changing diagnostic portions, and since portions to be diagnosed and the number thereof in the series of examinations may be different depending on facilities such as hospitals or the like, an operation performed by an operator is complicated in the present circumstances. For example, even though the diagnostic portion specifying patterns are arranged in the vicinity of the operation selecting unit according to the diagnosis order, at the time of proceeding to the next examination, an operator who has little experience in the facility employed, for example, owing to be a part-time worker, may mistakenly repeat an examination that is already executed, or may overlook a scheduled examination and may proceed to an examination to be executed after the next examination.

Further, the titles of examinations that are prepared in the ultrasound diagnostic apparatus often include titles accompanied with the names of the examination portions. For example, in a case where a blood vessel is an examination portion, generally, many blood vessels lack unity in their names, and accordingly, the name used in a facility such as a hospital or the like and the name registered in an ultrasound diagnostic apparatus are different from each other in some cases, which easily causes an operational error.

An object of the invention is to provide an ultrasound diagnostic apparatus that is capable of accurately executing a series of examinations even by an unskilled operator.

In order to attain the above-described object, the present invention provides an ultrasound diagnostic apparatus in which an ultrasonic wave is transmitted toward a subject by an ultrasound probe, an ultrasound image is generated by a diagnostic apparatus body based on reception data thus obtained and an examination is performed based on the ultrasound image, comprising a display unit on which a plurality of examination portions corresponding to a series of examinations relating to ultrasound diagnosis are displayed in an order of time series in a single screen at a time; and a controller which highlights an examination portion corresponding to an examination being executed among the plurality of examination portions in the display unit, wherein each of the plurality of examination portions is displayed as a body mark which indicates an examination position by the ultrasound probe.

In execution of the series of examinations, preferably, after an examination of an examination portion which is executed by freezing an ultrasound image is finished, the controller switches highlighting of a body mark of the examination portion to another body mark of an examination portion which next undergoes an examination, when freezing of the ultrasound image is released, or preferably, the controller switches highlighting of a body mark of the examination portion to another body mark of an examination portion which next undergoes an examination, when imaging mode is switched.

The ultrasound diagnostic apparatus may further comprise a selecting unit by which an operator selects one body mark from among a series of body marks displayed on the display unit, and if one body mark is selected through the selecting unit, the controller may switch highlighting of body marks starting from the selected body mark in an order of time series.

If a later body mark is selected through the selecting unit while leaving body marks of examination portions which have not yet undergone examinations, the controller may skip the body marks of examination portions which have not yet undergone examinations and switch highlighting of body marks starting from the selected later body mark in an order of time series.

If a body mark of an examination portion which has already undergone an examination is selected through the selecting unit, the controller may switch highlighting of body marks starting from the selected body mark among the series of body marks in an order of time series.

If a body mark which is not included in the series of examinations is selected through the selecting unit in the middle of the series of examinations, the controller may interrupt the series of examinations and highlight the selected body mark on the display unit, and if an examination corresponding to the selected body mark is finished, the controller may return to the series of examinations.

Preferably, the display unit and the selecting unit are configured by a touch panel.

It is preferable that the ultrasound diagnostic apparatus further comprises an image display unit, in which the ultrasound image is displayed on the image display unit together with the body mark corresponding thereto.

The body mark is one in which a probe mark indicating a position and a direction on which the ultrasound probe is put is superimposed and displayed on a body pattern which is a patterning of a body part seen in a predetermined direction.

The body mark may be one in which a mark indicating a position of a suspected region is superimposed and displayed on a body pattern which is a patterning of a specific organ.

Preferably, the body pattern in the body mark is changeable by an operation of an operator, and the probe mark or the mark indicating a position of a suspected region which is superimposed on the body pattern is movable and rotatable on the body pattern by an operation of the operator.

According to the invention, in ultrasound diagnosis, it is possible to easily recognize the flow of operations and to reduce the number of steps in operations. Thus, it is possible to accurately execute a series of examinations even though an operator is unskilled.

DETAILED DESCRIPTION OF THE INVENTION

Figure 1:
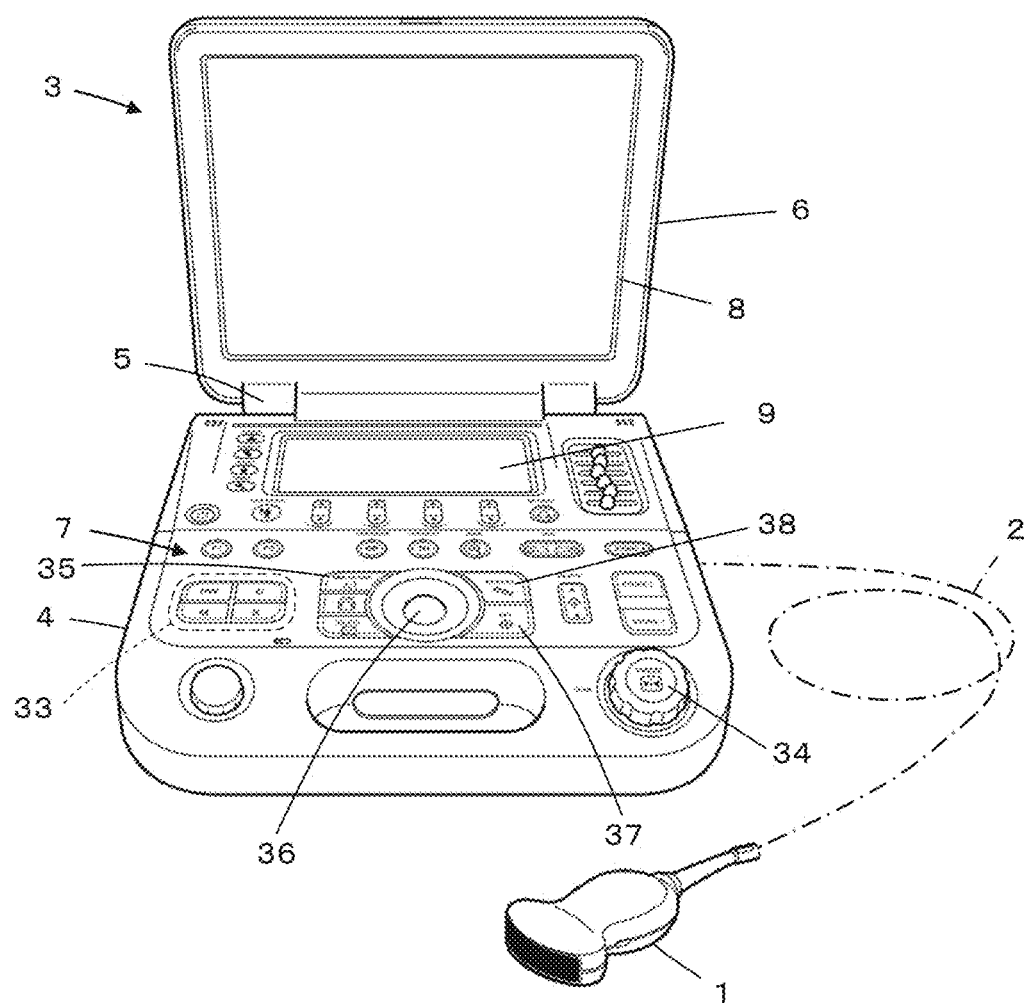
FIG. 1 is a perspective view illustrating an ultrasound diagnostic apparatus according to a first embodiment of the invention.

Hereinafter, embodiments of the invention will be described with reference to the accompanying drawings.
First Embodiment FIG. 1 shows the configuration of an ultrasound diagnostic apparatus according to a first embodiment of the invention. The ultrasound diagnostic apparatus includes an ultrasound probe 1 and a diagnostic apparatus body 3 connected to the ultrasound probe 1 through a communication cable 2.

The ultrasound diagnostic apparatus body 3 includes a housing 4 and a cover 6 that is rotatably installed at an end of the housing 4 through a hinge unit 5. The housing 4 has a substantially flat plate shape, and an operating unit 7 for various operations by an operator is formed on the surface thereof. A touch panel 9 is installed in the operating unit 7 on the side of the hinge unit 5. The cover 6 also has a substantially flat plate shape, and an image display unit 8 is formed on an inner surface thereof. The image display unit 8 faces the operating unit 7 of the housing 4 with the rotational moving by the hinge unit 5.

The operating unit 7 includes an imaging mode selecting button 33 for selecting an imaging mode, a freeze button 34 for imaging, a body mark button 35 for calling up a body mark registered in the diagnostic apparatus body 3 in advance onto the touch panel 9, a track ball 36 that is used for cursor operation, diagnosis or the like, a set button 37, a measure button 38, and the like. As the imaging mode selecting button 33, a B mode button for performing a B (brightness) mode imaging, a PW mode button for performing a PW (pulse wave-Doppler) mode imaging, a CF mode button for performing a CF (color flow) mode imaging, and the like are disposed.

Figure 2:
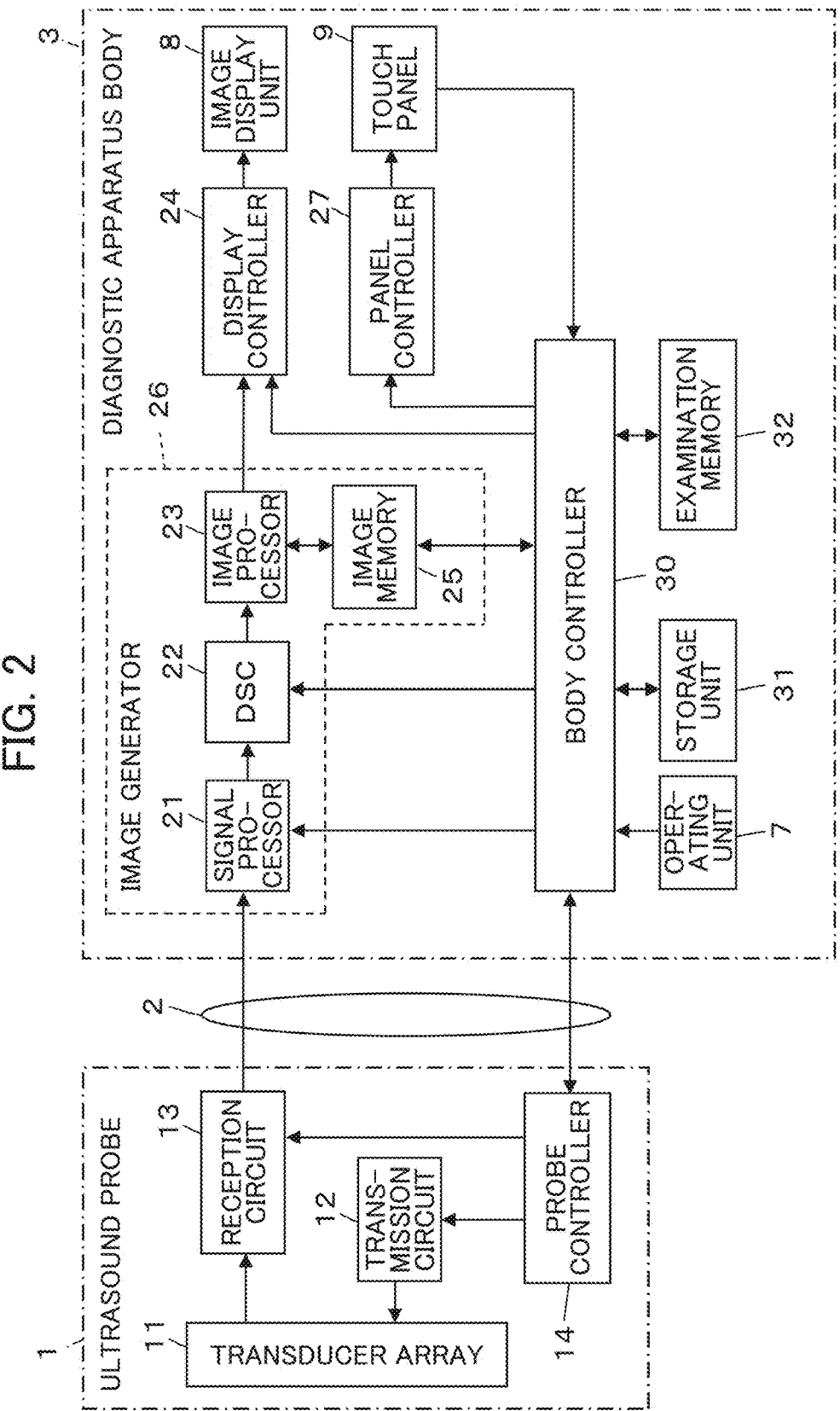
FIG. 2 is a block diagram illustrating an internal configuration of the ultrasound diagnostic apparatus according to the first embodiment.

Here, internal configurations of the ultrasound probe 1 and the diagnostic apparatus body 3 are shown in FIG. 2.

The ultrasound probe 1 has a transducer array 11, and a transmission circuit 12 and a reception circuit 13 are connected to the transducer array 11. A probe controller 14 is connected to the transmission circuit 12 and the reception circuit 13.

The diagnostic apparatus body 3 has a signal processor 21 which is connected to the reception circuit 13 through the communication cable 2. A DSC (Digital Scan Converter) 22, an image processor 23, a display controller 24, and an image display unit 8 are sequentially connected to the signal processor 21. An image memory 25 is connected to the image processor 23, and the signal processor 21, the DSC 22, the image processor 23 and the image memory 25 constitute an image generator 26. A panel controller 27 is connected to the touch panel 9.

In addition, a body controller 30 is connected to the signal processor 21, the DSC 22, the display controller 24, the image memory 25 and the panel controller 27, and the operating unit 7, a storage unit 31, an examination memory 32 and the touch panel 9 are respectively connected to the body controller 30.

The probe controller 14 of the ultrasound probe 1 and the body controller 30 of the diagnostic apparatus body 3 are connected to each other through the communication cable 2.

The transducer array 11 of the ultrasound probe 1 has a plurality of ultrasound transducers arranged in a shape of a one-dimensional or two-dimensional array. According to a driving signal supplied from the transmission circuit 12, each of the ultrasound transducers transmits an ultrasonic wave toward a subject and also receives an ultrasonic echo from the subject to output the reception signal. Each ultrasound transducer is configured by a vibrator in which electrodes are formed at both ends of the piezoelectric body comprising, for example, a piezoelectric ceramic represented by PZT (lead zirconate titanate), a piezoelectric polymer element represented by PVDF (polyvinylidene fluoride), a piezoelectric single crystal represented by PMN-PT (lead magnesium niobate-lead titanate solid solution), or the like.

When a pulsed or continuous-wave voltage is applied to the electrodes of the respective vibrators, the piezoelectric body expands and contracts, and the respective vibrators generate pulsed or continuous-wave ultrasonic waves. By combining these ultrasonic waves, an ultrasound beam is formed. Also, when the respective vibrators receive propagated ultrasonic waves, they expand and contract, thereby generating electric signals. These electric signals are output as reception signals of the received ultrasonic waves.

The transmission circuit 12 includes, for example, a plurality of pulsers. The transmission circuit 12 adjusts the amount of delay of each driving signal on the basis of the transmission delay pattern, which is selected depending on the control signal from the probe controller 14, so that ultrasonic waves transmitted from the plurality of ultrasound transducers of the transducer array 11 form an ultrasound beam, and supplies the adjusted driving signals to the plurality of ultrasound transducers.

The reception circuit 13 performs amplification and A/D conversion of the reception signals transmitted from the respective ultrasound transducers of the transducer array 11, and then performs a reception focusing processing by giving and adding a delay to each of the reception signals in accordance with a sound velocity or a distribution of sound velocity which is set on the basis of a reception delay pattern selected depending on the control signal from the probe controller 14. Through this reception focusing processing, reception data (sound ray signal) in which the focus of the ultrasonic echo is narrowed down is generated.

The probe controller 14 controls individual unit of the ultrasound probe 1 on the basis of various control signals transmitted from the body controller 30 of the diagnostic apparatus body 3.

The signal processor 21 of the diagnostic apparatus body 3 generates a B-mode image signal, which is tomographic image information regarding tissue within the subject, by performing correction of attenuation on the basis of distance on the reception data generated by the reception circuit 13 of the ultrasound probe 1 depending on the depth of the reflection position of the ultrasonic wave and then performing envelope detection processing on the reception data subjected to correction of attenuation.

The DSC 22 converts the B-mode image signal generated by the signal processor 21 into an image signal according to the normal television signal scanning method (raster conversion).

The image processor 23 performs various kinds of required image processing, such as gradation processing, on the B-mode image signal input from the DSC 22 and then outputs the B-mode image signal to the display controller 24, or stores the B-mode image signal in the image memory 25.

The display controller 24 displays an ultrasound image on the image display unit 8 on the basis of the B-mode image signal subjected to image processing by the image processor 23.

The image display unit 8 includes a display device, for example, such as an LCD or the like, and displays the ultrasound image under the control of the display controller 24. When an examination is performed, a cursor, a caliper or the like for examination is superimposed and displayed on the ultrasound diagnostic image as necessary.

The operating unit 7 is disposed on the surface of the housing 4 and as described above, includes various operation buttons for input operations by an operator.

The storage unit 31 stores an operation program, an examination program including a series of examinations and the examination portions corresponding thereto, and the like. As the storage unit 31, recording media, such as a hard disk, a flexible disk, an MO, an MT, a RAM, a CD-ROM, a DVD-ROM, an SD card, a CF card, and a USB memory, or a server may be used.

The examination memory 32 is a memory in which information relating to an examination result obtained by the examination, such as measurement values and the like, is stored.

The body controller 30 controls individual unit in the diagnostic apparatus body 3 on the basis of the various instruction signals and the like input from the operating unit 7 by the operator.

Although the signal processor 21, the DSC 22, the image processor 23, the display controller 24 and the panel controller 27 are realized by a CPU and an operation program which causes the CPU to execute various kinds of processing, they may also be formed using digital circuits.

The panel controller 27 displays operation display image of the series of examinations or the examination portions corresponding thereto that is output from the body controller 30 on the touch panel 9. As the operation display image corresponding to the examination portion, for example, a body mark in which a probe mark indicating a position and a direction on which the ultrasound probe 1 is put is superimposed and displayed on a body pattern which is a patterning of a part of the body seen in a predetermined direction may be used.

The touch panel 9 is a device having both of display function and position input function. For example, the touch panel 9 is composed of a display device such as an LCD or the like and a transparent film sensor pasted thereon that senses a touch or the like of the operator. The touch panel 9 outputs a predetermined operation signal on the basis of a display on the display device, a touch position on the film sensor and the like. As the detection system in the film sensor, an appropriate system such as a resistive film system or an electrostatic capacitance system may be used.

The operation input by the touch panel 9 is output as an operation signal to the body controller 30, and a predetermined operation is performed by the body controller 30.

Instead of the touch panel 9, an operation display unit and an operation selecting unit may be respectively provided.

Next, the action of the first embodiment will be described.

By turning on a power switch disposed in the operating unit 7 of the housing 4 of the diagnostic apparatus body 3, electric power is supplied to each unit in the diagnostic apparatus body 3 and the ultrasound probe 1, and thus, the ultrasound diagnostic apparatus is started up.

Figure 3:
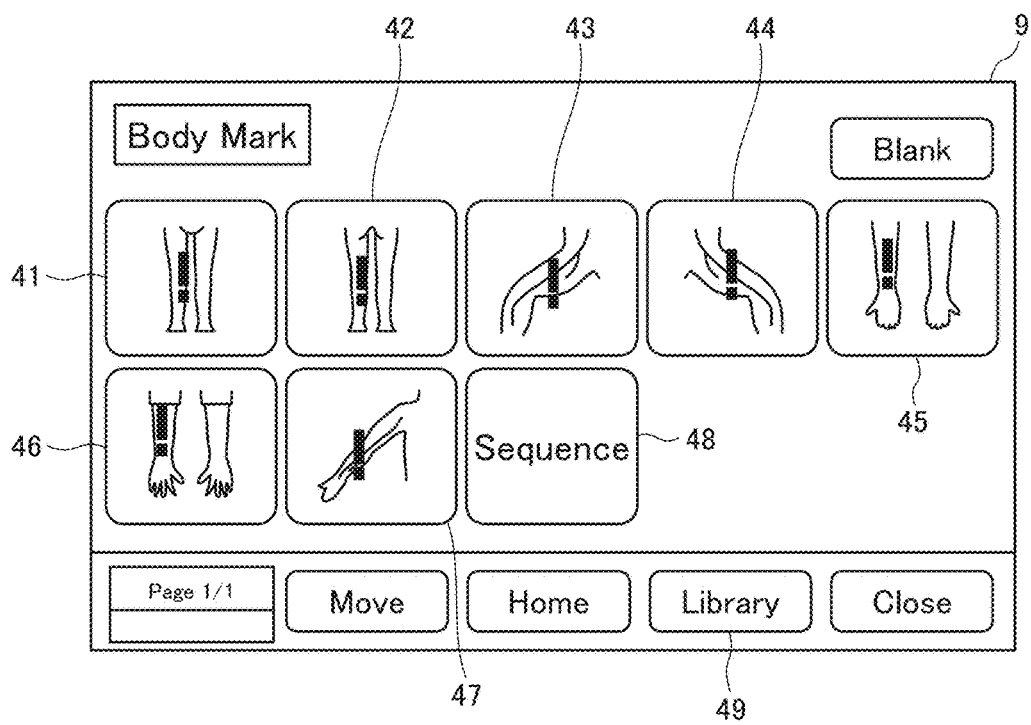
FIG. 3 is a diagram illustrating an example of a body mark selecting screen in the first embodiment.

First, the body mark button 35 of the operating unit 7 is pushed by the operator. The body controller 30 detects that the body mark button 35 is pushed, calls up body marks 41 to 47 that are stored in the storage unit 31 and that correspond to the examination portions of the ultrasound diagnosis and a sequence button 48 that is also stored in the storage unit 31 and that makes the body marks 41 to 47 corresponding to the series of examinations to be displayed in the order of time series, and displays the body marks 41 to 47 and the sequence button 48 on the touch panel 9 through the panel controller 27, as illustrated in FIG. 3.

Figure 4:
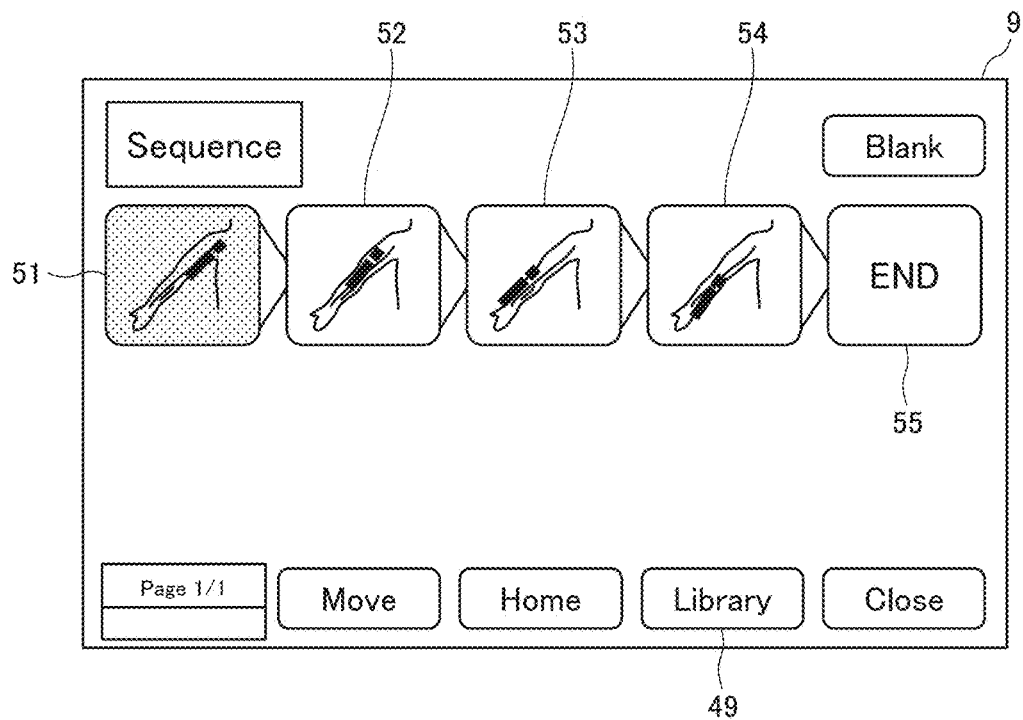
FIG. 4 is a diagram illustrating an example of a sequence display of body marks corresponding to a series of examinations in the first embodiment.

Then, if the sequence button 48 that is displayed on the touch panel 9 is selected by the operator in order to perform the series of examinations, the body controller 30 detects that the sequence button 48 displayed on the touch panel 9 is selected, calls up a series of body marks 51 to 54 corresponding to the series of examinations and an end button 55 that are stored in the storage unit 31, and displays (sequence-displays) the body marks 51 to 54 and the end button 55 in the order of time series on the touch panel 9 through the panel controller 27, as illustrated in FIG. 4.

Here, the series of body marks 51 to 54 shown in FIG. 4 relates to the examination of the artery of upper extremity (right), in which the body mark 51 corresponds to the examination of the axillary artery (right), the body mark 52 corresponds to the examination of the biachial artery (right), the body mark 53 corresponds to the examination of the radial artery (right), and the body mark 54 corresponds to the examination of the ulnar artery (right), respectively. The operator checks the presence or absence of stenosis of vascular or the presence or absence of blood clot by the series of examinations, or, for example, compares the state of vascular after operation with the state of vascular before operation in a case where an internal shunting in dialysis is performed.

Figure 5:
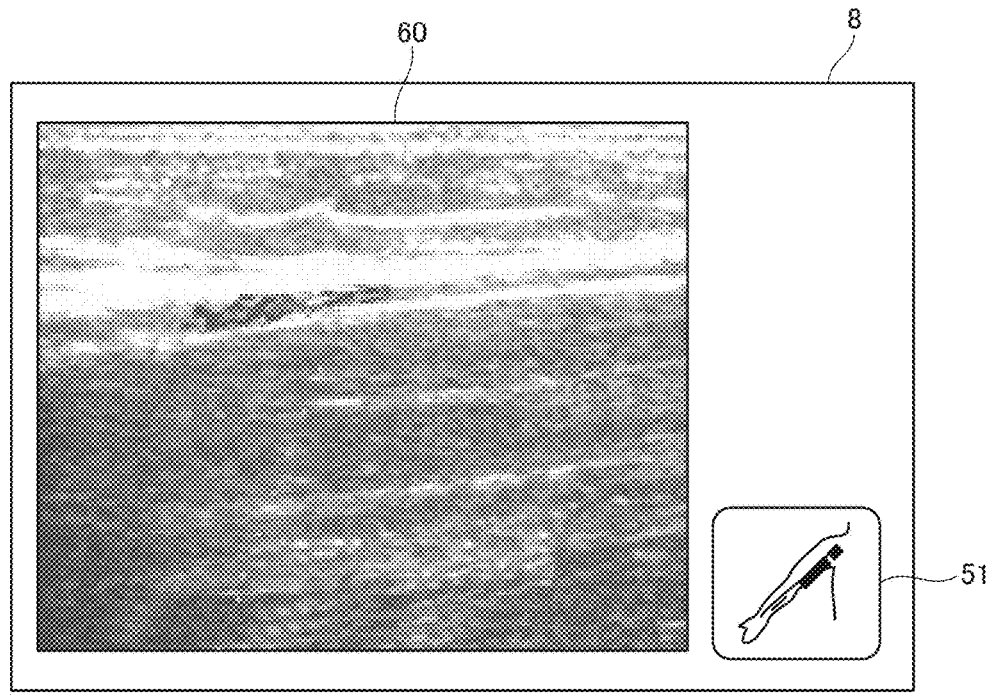
FIG. 5 is a diagram illustrating an example of a screen display in the first embodiment that includes an ultrasound diagnostic image and a body mark display corresponding thereto.

The series of examinations is started in the order of the sequence display displayed on the touch panel 9 by the operator. As illustrated in FIG. 4, the body mark 51 corresponding to the first examination displayed on the touch panel 9 is highlighted by the body controller 30 through the panel controller 27 so that the operator can recognize the examination that is currently performed. Further, as illustrated in FIG. 5, the body mark 51 corresponding to the examination that is currently performed is displayed on the image display unit 8 together with the ultrasound image through the display controller 24. The display position of the body mark on the image display unit 8 may be changed into an arbitrary position through the operating unit 7. In a case where there is room in the display space of the image display unit 8, the ultrasound image and the body mark may be displayed in parallel in the display space that is prepared in advance, and in a case where there is little free space in the display space of the image display unit 8, the body mark may be superimposed and displayed on a portion of the ultrasound image where there is no influence on the ultrasound image diagnosis.

Further, various known methods may be applied to the highlighting, such as a method in which the body mark to be highlighted itself is made to flash or a method in which the contour of the body mark to be highlighted is thickened, in addition to a method in which the color of the body mark to be highlighted is made different from the color of the other body marks.

The ultrasound diagnosis is started by the operator. As illustrated in FIG. 5, the operator confirms the body mark 51 that is displayed on the image display unit 8, positions the ultrasound probe 1 at a predetermined position of the subject corresponding to the body mark 51, and in this state, starts the B mode imaging.

In a case where an initial setting is made so that the B mode imaging is automatically selected when the ultrasound diagnostic apparatus is started up, it is possible to start the B mode imaging without operating the imaging mode selecting button 33 of the operating unit 7. On the other hand, in a case where the initial setting is not made so that the B mode imaging is selected, or in a case where the B mode imaging is performed after an imaging other than the B mode imaging is performed, it is possible to start the B mode imaging by operating the imaging mode selecting button 33 of the operating unit 7.

If the B mode imaging is started as described above, a B mode image captured by the ultrasound probe 1 is displayed on the image display unit 8 as a moving image in real time. More specifically, the body controller 30 controls the probe controller 14 so that the transmission circuit 12 of the ultrasound probe 1 outputs a drive signal, the plurality of ultrasound transducers of the transducer array 11 sequentially transmits ultrasound beams, and the respective ultrasound transducers receive reception signals and output the reception signals to the reception circuit 13 to generate reception data. The image generator 26 of the diagnostic apparatus body 3 generates an image signal on the basis of the reception data, and the display controller 24 displays the B mode image on the image display unit 8 on the basis of the image signal.

Next, if the freeze button 34 of the operating unit 7 is pushed by the operator, the body controller 30 detects that the freeze button 34 is pushed, stores the B mode image data, which is still image data when the freeze button 34 is pushed, in the image memory 25, and also displays the B mode image 60 on the image display unit 8 through the display controller 24, as illustrated in FIG. 5.

With respect to the B mode image 60 that is displayed on the image display unit 8, a predetermined examination is performed by the operator. For example, the track ball 36, the set button 37 and the measure button 38 of the operating unit 7 are operated by the operator to perform the examination on the basis of the B mode image 60 that is displayed on the image display unit 8. In response to the operation by the operator input from the operating unit 7, the body controller 30 stores the image data of the B mode image 60 that is displayed on the image display unit 8 in the image memory 25. In addition, the body controller 30 correlates the examination result in the examination performed by the operator and the information on the body mark 51 which is displayed together with the B mode image 60 with the information on the image data of the B mode image 60 stored in the image memory 25, and stores the resultant in the examination memory 32.

In this embodiment, the above-mentioned imaging, examination and data storage are performed with respect to a B mode image, but the invention is not limited thereto. For example, imaging of a ultrasound image other than the B mode image such as a PW mode image or a CF mode image may be performed, and an examination including measurement or the like may be performed for the ultrasound image, and similarly to the case of the B mode image, image data of the ultrasound image may be stored in the image memory 25, and the examination result and the information on the body mark 51 correlated with the information on the image data stored in the image memory 25 may be stored in the examination memory 32.

As image data of an ultrasound image is appropriately correlated with a body mark and an examination result and then stored, in a case where an operator reconfirms the ultrasound image later or in a case where a third person confirms the ultrasound image, it is possible to easily grasp the examination portion and the state of observation corresponding to the ultrasound image.

Figure 6:
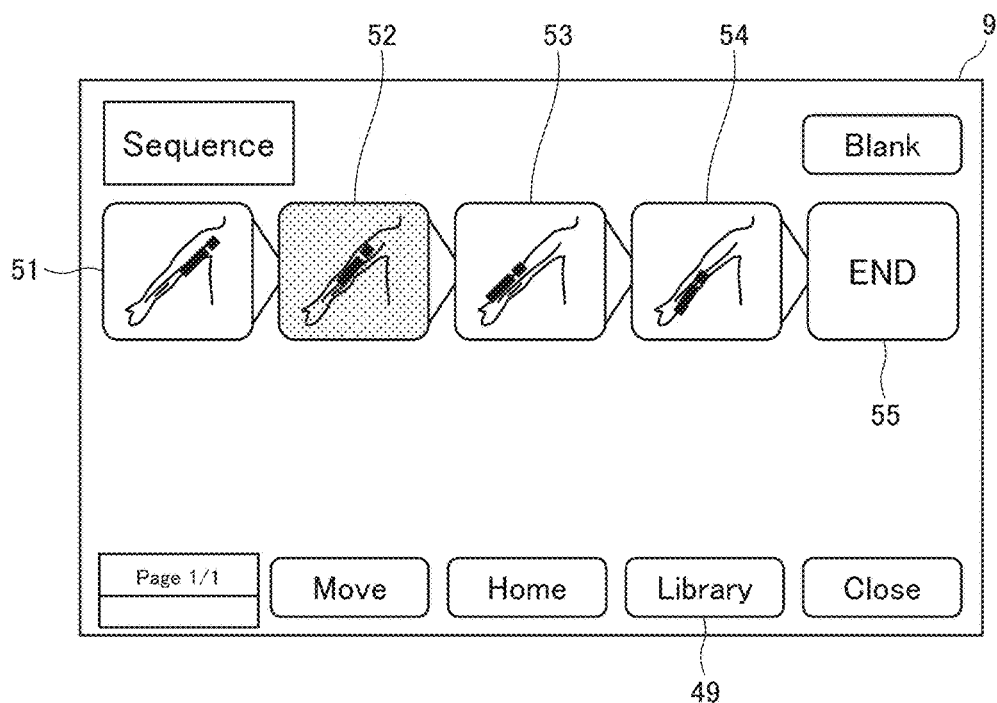
FIG. 6 is a diagram illustrating a sequence display in a case where highlighting in FIG. 4 is switched.

If all the examinations are finished with respect to the examination portion indicated by the body mark 51, the freeze button 34 of the operating unit 7 is pushed again by the operator. The body controller 30 detects that the freeze button 34 is pushed, and releases the freezing of the captured image. Then, as illustrated in FIG. 6, the body controller 30 releases the highlighting of the body mark 51 displayed on the touch panel 9 and newly highlights the next body mark 52 through the panel controller 27, and also switches the body mark 51 displayed on the image display unit 8 to the body mark 52 through the display controller 24. In this way, the series of body marks that are sequence-displayed on the touch panel 9 are sequentially switched in highlighting in the order of time series corresponding to the state of proceeding of the series of examinations, and the display of the body mark corresponding to the highlighting on the image display unit 8 is also sequentially switched.

The operator starts a new examination corresponding to the body mark 52 that is highlighted by the touch panel 9. Similarly to the case of the body mark 51, the operator confirms the body mark 52 that is displayed on the image display unit 8, positions the ultrasound probe 1 at the predetermined position of the subject corresponding to the body mark 52, and in this state, pushes the imaging mode selecting button 33 of the operating unit 7. Operations thereafter are the same as in the case of the body mark 51.

In this way, according to the series of body marks 51 to 54 in which the highlighting is sequentially switched in the order of time series, the ultrasound diagnoses by the operator are executed, and when the ultrasound diagnosis corresponding to the final body mark 54 is finished, the end button 55 on the touch panel 9 is pushed and thus, all the examinations are finished.

In the ultrasound diagnostic apparatus according to the first embodiment, the series of body marks corresponding to the series of examination portions are sequence-displayed on the touch panel 9, the highlighting of the body marks is sequentially switched in the order of time series according to the status of implementation of the examination, and the body mark corresponding to the examination is displayed on the image display unit 8. Accordingly, it is possible to prevent that an examination that is already executed is mistakenly repeated, or to prevent that a scheduled examination is overlooked and an examination to be executed after the scheduled examination is executed. In addition, since the highlighted body mark is automatically correlated with the ultrasound image captured in the ultrasound diagnosis, it is not necessary for the operator to manually operate the diagnostic apparatus body 3 to correlate the body mark with the ultrasound image in each examination of the series of examinations, and thus, it is possible to reduce the number of steps in the operations as a whole.

Second Embodiment

Next, a second embodiment of the invention will be described.

The configuration of an ultrasound diagnostic apparatus according to the second embodiment is the same as that of the first embodiment illustrated in FIGS. 1 and 2.

Figure 7:
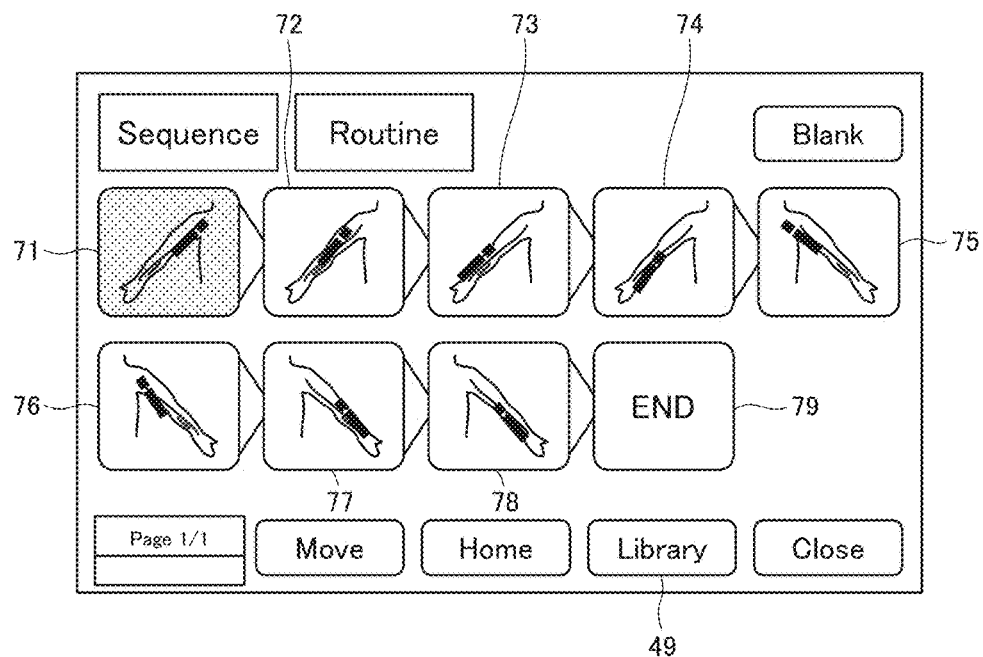
FIG. 7 is a diagram illustrating an example of a sequence display of body marks corresponding to a series of examinations in a second embodiment of the invention.

At the time of ultrasound diagnosis, if the sequence button 48 that is displayed on the touch panel 9 illustrated in FIG. 3 is selected by the operator, the body controller 30 detects that the sequence button 48 is selected, calls up a series of routine examinations relating to the artery of upper extremity that is stored in advance in the storage unit 31, for example, and sequence-displays body marks 71 to 78 and an end button 79 on the touch panel 9 through the panel controller 27, as illustrated in FIG. 7.

Figure 8:
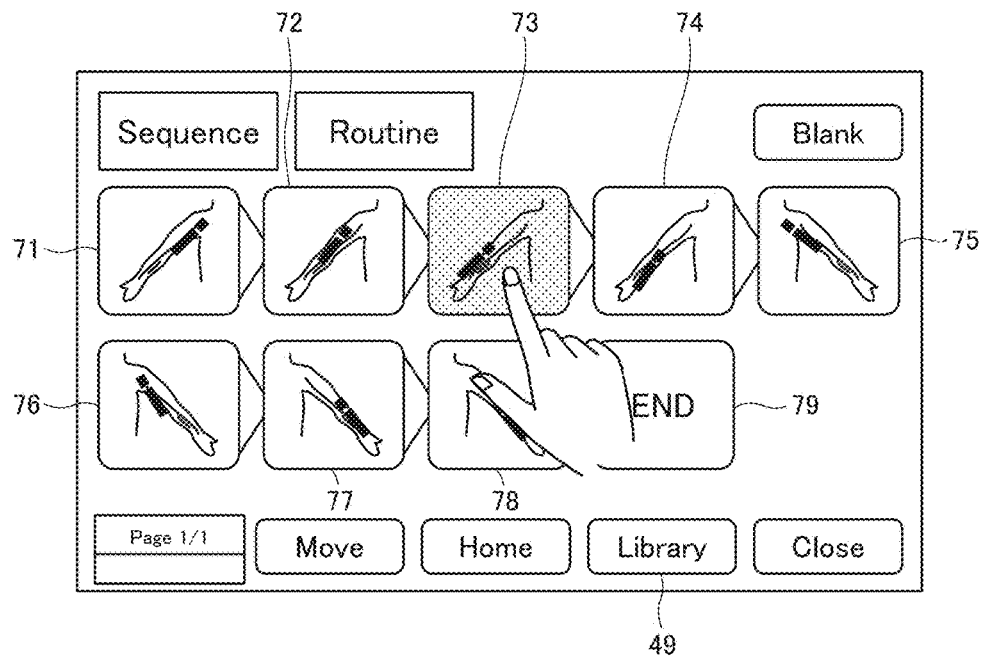
FIG. 8 is a diagram illustrating an example of a sequence display in a case where a predetermined body mark in FIG. 7 is selected as a starting position.

Further, before the ultrasound diagnosis is started, for example, if the body mark 73 which corresponds to an examination in the middle of the series of examinations is selected by the operator from among the body marks 71 to 78 sequence-displayed on the touch panel 9, as illustrated in FIG. 8, the body controller 30 detects that the body mark 73 is selected, controls the touch panel 9 through the panel controller 27 so that the highlighting of the body mark 71 is released and the body mark 73 is highlighted, and switches the display of the body mark on the image display unit 8 from the body mark 71 to the body mark 73 through the display controller 24. In response to this, the operator can sequentially perform the examinations from the examination corresponding to the body mark 73 by changing the starting position of the series of examinations from the body mark 71 into the body mark 73.

Figure 9:
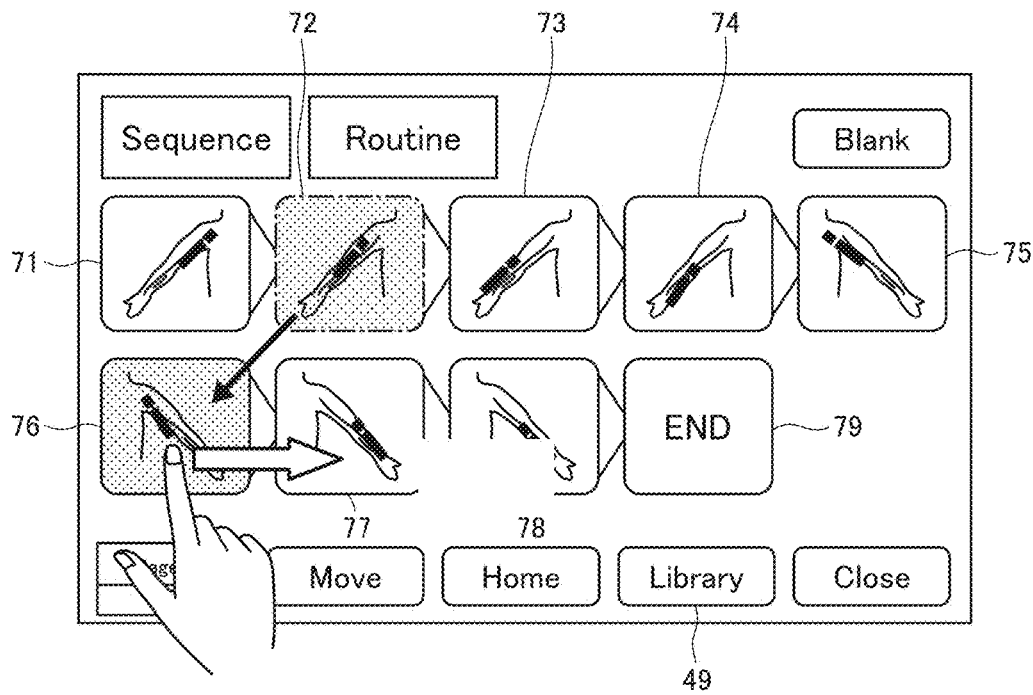
FIG. 9 is a diagram illustrating an example of a sequence display in a case where body marks in the middle of sequence are skipped in FIG. 7.

Further, for example, in a state where the body mark 72 is highlighted, if the later body mark 76 is selected by the operator from among the body marks 71 to 78 sequence-displayed on the touch panel 9 while leaving the body marks 72 to 75 corresponding to examinations all of which are not executed yet, as illustrated in FIG. 9, the body controller 30 detects that the body mark 76 is selected, controls the touch panel 9 through the panel controller 27 so that the highlighting of the body mark 72 is released and the body mark 76 is highlighted, and switches the display of the body mark on the image display unit 8 from the body mark 72 to the body mark 76 through the display controller 24. In response to this, the operator can sequentially perform the examinations from the examination corresponding to the body mark 76 while skipping a part of the series of examinations corresponding to the body marks 72 to 75 which is not completely executed.

Similarly, if a body mark corresponding to an examination which is already executed is selected by the operator from among the body marks sequence-displayed on the touch panel 9, the body controller 30 detects that the body mark corresponding to the examination already executed is selected, controls the touch panel 9 through the touch controller 27 so that the selected body mark corresponding to the examination already executed is highlighted again, and switches the display of the body mark on the image display unit 8 to the body mark corresponding to the examination already executed through the display controller 24. In response to this, the operator can sequentially perform the examinations from the examination corresponding to the re-highlighted body mark.

Third Embodiment

Next, a third embodiment of the invention will be described.

A configuration of an ultrasound diagnostic apparatus according to the third embodiment is the same as those of the first and second embodiments.

In the series of examinations in the first and second embodiments, the body controller 30 detects that the freeze button 34 is pushed again and performs switching of the highlighting of the body mark in a predetermined timing when the freezing of the ultrasonic image is released, but the invention is not limited thereto. The body controller 30 may detect that the imaging mode selecting button 33 is pushed and may perform switching of the highlighting of the body mark in a predetermined timing when the imaging mode is switched, instead of performing the switching in a predetermined timing when the freezing of the ultrasonic image is released.

For example, in ultrasound diagnosis, in a case where a B mode image is obtained and then a PW mode image is obtained at a predetermined position on the basis of the B mode image, the operator finishes the ultrasound diagnosis by means of the PW mode image, pushes the freeze button 34 again to release the freezing of the PW mode image, and finishes one examination. Then, the operator starts a new examination, and pushes the B mode button of the imaging mode selecting button 33.

Accordingly, in the above-mentioned case, the body controller 30 may detect that the B mode button is pushed, and may perform the switching of the highlighting of the body mark on the touch panel 9 and the switching of the display of the body mark on the image display unit 8 in the timing when the imaging mode is switched.

Fourth Embodiment

Next, a fourth embodiment of the invention will be described.

A configuration of an ultrasound diagnostic apparatus according to the fourth embodiment is the same as those of the first, second and third embodiments.

The body marks including body patterns that are sequence-displayed on the touch panel 9 corresponding to the series of examinations and probe marks that are superimposed and displayed on the body patterns are stored in the storage unit 31 of the diagnostic apparatus body 3 in advance.

At the time of ultrasound diagnosis, it is possible for the operator to newly assemble a sequence display which corresponds to predetermined examinations by rearranging the order of the body marks corresponding to the series of examinations that are sequence-displayed on the touch panel 9 illustrated in FIGS. 7 to 9, or, by calling up a different body mark (or different body marks) to replace a part of the body marks corresponding to the series of examinations illustrated in FIGS. 7 to 9 with the different body mark (or the different body marks) or to add the different body mark (or the different body marks) to the body marks corresponding to the series of examinations illustrated in FIGS. 7 to 9.

The sequence display of the body marks corresponding to the series of examinations that are newly assembled may be stored in the storage unit 31 through the operating unit 7 and the body controller 30.

In a case where abnormality is found in a predetermined examination portion in the middle of the series of examinations, the operator may select a library button 49 illustrated in FIGS. 7 to 9 to select a body mark that defines the examination portion in more detail, and may temporarily interrupt the series of examinations to perform a specific examination.

Figure 10:
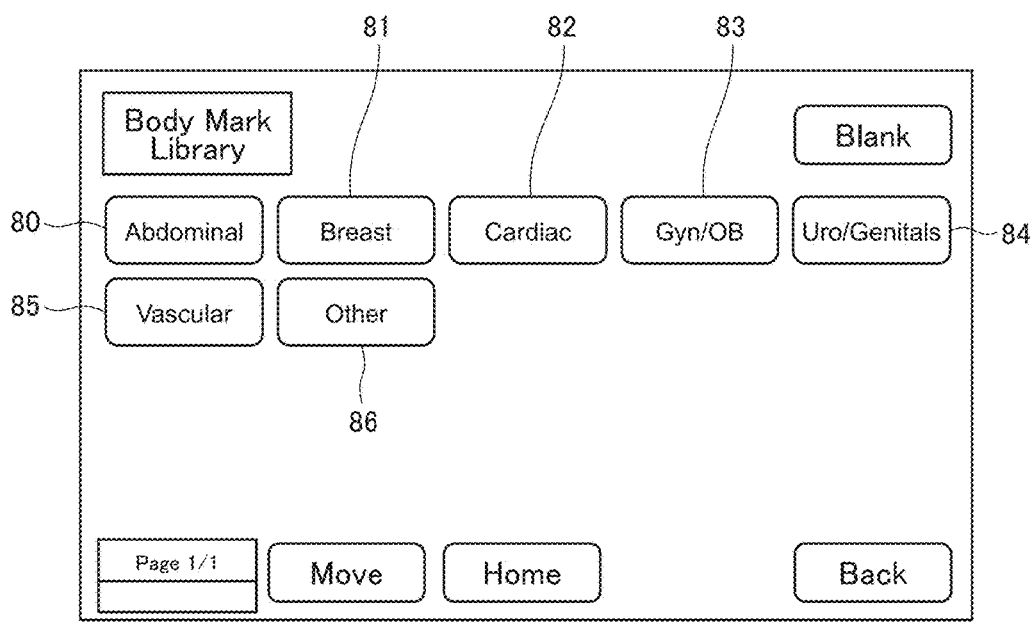
FIG. 10 is a diagram illustrating an example of a library category selecting screen displayed on a touch panel in a case where a library button is selected.
Figure 11:
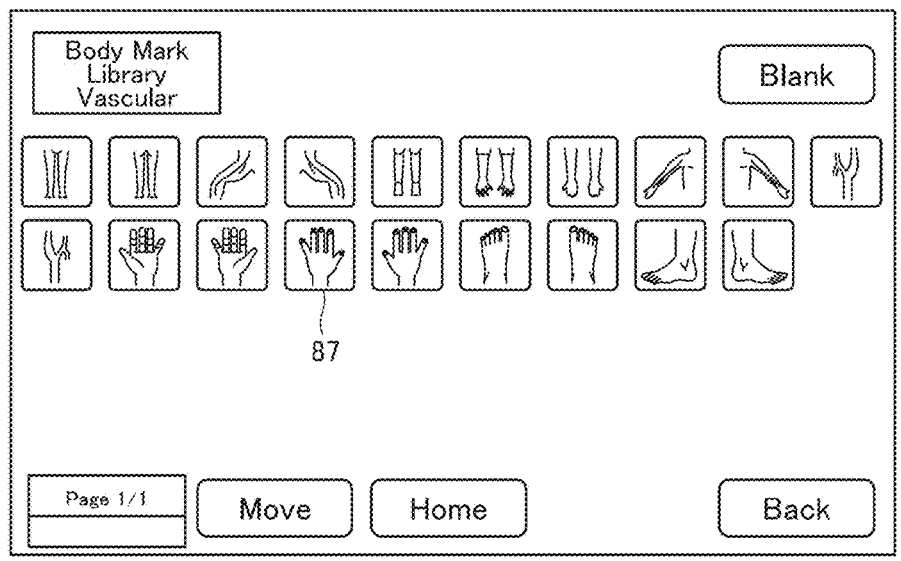
FIG. 11 is a diagram illustrating an example of a library screen of a vascular category.

For example, in a case where abnormality is found in the examination corresponding to the body mark 74 among the series of examinations that are sequence-displayed on the touch panel 9 illustrated in FIG. 9, the operator selects the library button 49 to make a library category selecting screen illustrated in FIG. 10 to be displayed on the touch panel 9. The library category select screen includes category marks 80 to 86 that indicate categories of the body marks, for example. If a category mark 85 that indicates a vascular category is selected by the operator from among the category marks 80 to 86 that are displayed on the touch panel 9, the body controller 30 calls up body marks that belong to the vascular category from the storage unit 31, and as illustrated in FIG. 11, displays the body marks as a library of the vascular category on the touch panel 9 through the panel controller 27. The operator selects a body mark 87 which corresponds to a more detailed examination portion of the body mark 74, pushes the freeze button 34 to release the freezing of an ultrasound image, and performs a detailed examination separately from the series of examinations. The operator positions the ultrasound probe 1 at a predetermined position of a subject corresponding to the body mark 87 that is displayed on the image display unit 8, and pushes the freeze button 34 to display a corresponding ultrasound image on the image display unit 8. Similarly to the above, the body controller 30 correlates B mode image data, which is image data of a still image when the freeze button 34 is pushed, with the body mark 87, and stores the resultant in the image memory 25.

After the examination for the body mark 87 is performed, if the operator pushes the freeze button 34 to release the freezing of the ultrasonic image, the series of examinations illustrated in FIG. 9 is displayed again on the touch panel 9, and the series of examinations which has been interrupted is automatically started. The operator restarts the remaining examinations from the examination corresponding to body mark 75 which has been interrupted.

In a case where a desired body mark is not stored in the storage unit 31, the operator may create a new body mark comprising a combination of a body pattern and a probe mark that is superimposed and displayed on the body pattern by selecting the library button 49 and operating the operating unit 7.

If the library button 49 on the touch panel 9 illustrated in FIGS. 7 to 9 is selected by the operator, the body controller 30 detects that the library button 49 is selected, and displays the library category selecting screen illustrated in FIG. 10 on the touch panel 9. For example, if a category mark 80 indicating an abdominal category is selected by the operator, the body controller 30 calls up plural body marks that belong to the abdominal category, and displays the plural body marks as a library of the abdominal category on the touch panel 9 through the panel controller 27, as illustrated in FIG. 12.

Figure 12:
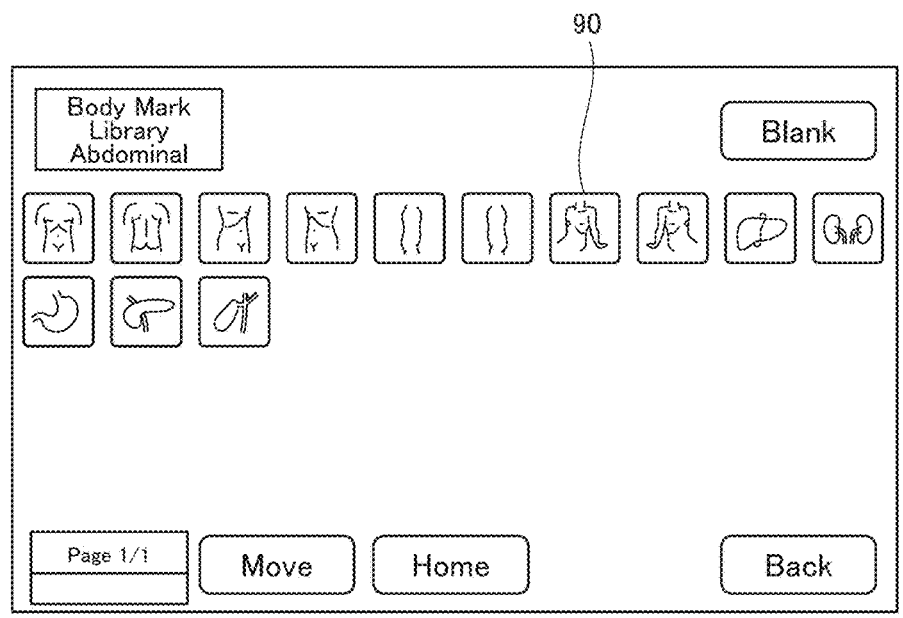
FIG. 12 is a diagram illustrating an example of a library screen of an abdominal category.

For example, the operator selects a body mark including a desired body pattern from the plural body marks belonging to the abdominal category that are displayed on the touch panel 9 illustrated in FIG. 12. For example, if a body mark 90 is selected by the operator, the body mark 90 in which a probe mark 92 is operably disposed at an arbitrary position of a corresponding body pattern 91 while being superimposed thereon is displayed on the image display unit 8, as illustrated in FIG. 13.

Figure 13:
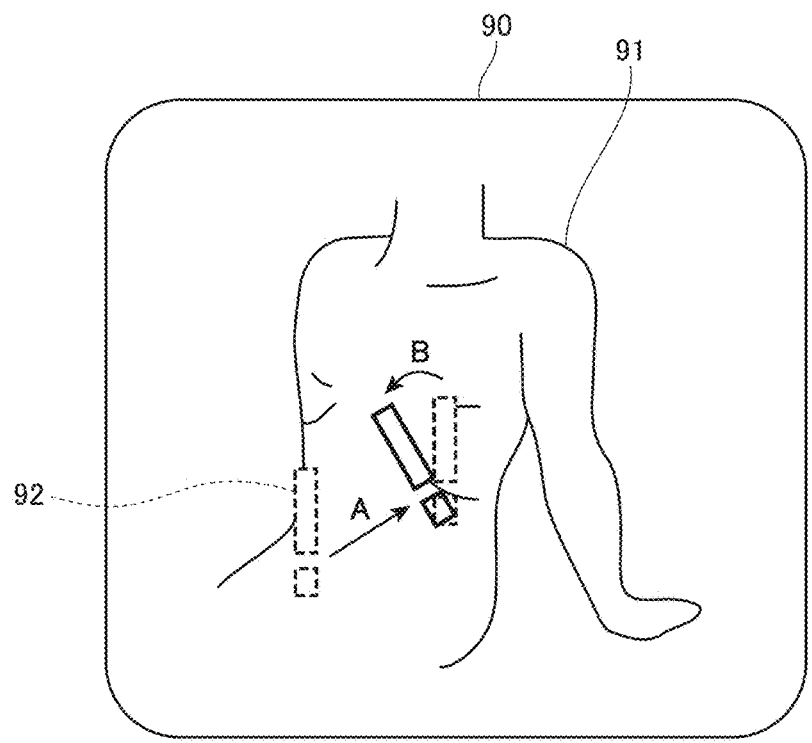
FIG. 13 is a diagram illustrating a body mark which is created in a fourth embodiment of the invention.

The operator operates the operating unit 7 to move the probe mark 92 parallel to the initial position thereof as indicated by operation A in FIG. 13 and to rotationally move the probe mark 92 and alter the angle thereof as indicated by operation B in FIG. 13, thereby making it possible to create the desired body mark 90.

The newly created body mark 90 may be stored in the storage unit 31, and as necessary, may be used in the sequence display to use as a display of an examination portion in the series of examinations.

In the above-described first to fourth embodiments, the sequence display including the series of body marks which corresponds to the series of examinations is displayed on the touch panel 9 and the body mark corresponding to the examination being executed is displayed on the image display unit 8. Since the operator performs the series of examinations by confirming the body mark displayed on the image display unit 8, it is preferable that at the time of switching the imaging mode, the body controller 30 controls the touch controller 27 to display on the touch panel 9 an operation screen corresponding to the imaging mode in which parameters of image processing or signal processing are disposed.

By operating the operation screen corresponding to the imaging mode displayed on the touch panel 9 to adjust the parameters of image processing or signal processing, it is possible to obtain an ultrasound image easy to observe in which parameters are appropriately adjusted for each imaging mode.

Figure 14:
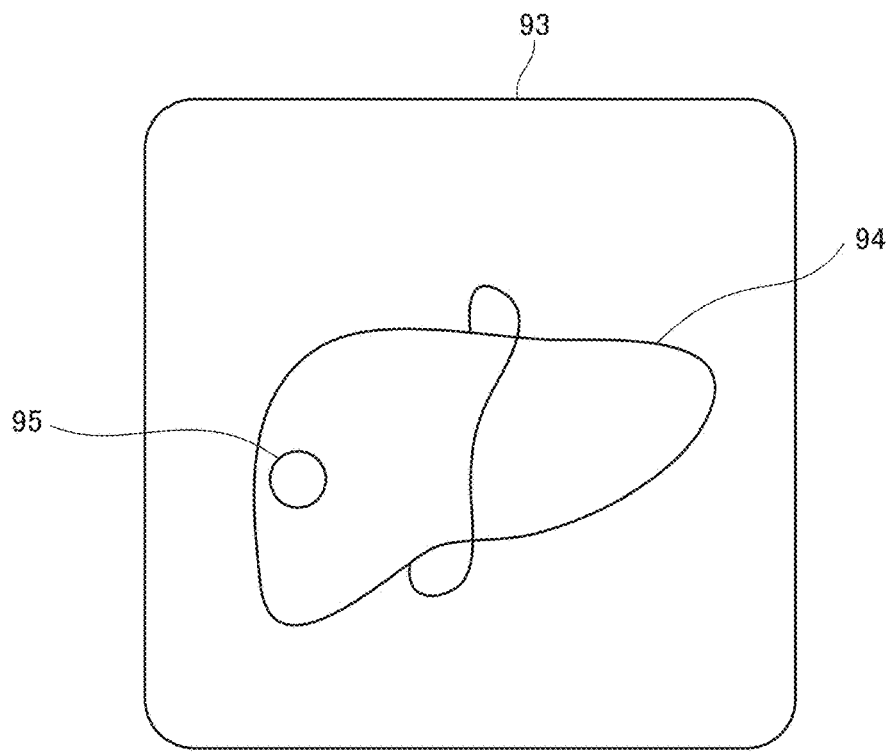
FIG. 14 is a diagram illustrating another example of the body mark, which is a body mark in which a mark indicating a position of a suspected region is superimposed and displayed on a body pattern which is a patterning of a specific organ.

Further, as described above, a body mark in which a probe mark indicating a position and a direction on which the ultrasound probe 1 is put is superimposed and displayed on a body pattern which is a patterning of a part of the body seen in a predetermined direction may be used as the body mark, but the body mark is not limited thereto. For example, the body mark may be one in which a mark indicating a position of a region suspected of having a tumor, a polyp, a stone or the like is superimposed and displayed on a body pattern which is a patterning of a specific organ, as illustrated in FIG. 14. In the body mark 93 illustrated in FIG. 14, a mark 95 indicating the position of a tumor is superimposed and displayed on a body pattern 94 of the liver.

Similarly to the above-described probe mark, the mark indicating a position a suspected region may be operable by an operator, and may be disposed on an arbitrary position.

While the ultrasound diagnostic apparatus according to the invention has been described in detail, the invention is not limited to the above-mentioned embodiments but may be improved or modified in a range without departing from the gist of the invention.

What is claimed is:

1. An ultrasound diagnostic method utilizing an ultrasound diagnostic apparatus including an ultrasound probe, comprising:
    performing an instruction signal input, using an operating unit of the ultrasound diagnostic apparatus, by an operator,
    displaying, in response to the instruction input signal operation by the operator, a plurality of first body marks on a first touch panel display screen at a time, each of the first body marks being different from each other in a body pattern which is a patterning of a body part seen in a predetermined direction, and being further superimposed on by a probe mark which indicates a position and a direction on the body pattern which the ultrasound probe is put,
    displaying, in response to the operator selecting, using the first touch panel display screen, one body mark from among the plurality of the first body marks a series of second body marks corresponding to a series of examinations relating to ultrasound diagnosis in an order of time on the first touch panel display screen, each of the second body marks relating to the selected first body mark, and the body patterns of the second body marks being the same for each other in the body pattern of the selected first body mark and being different, from each other in the position and the direction indicated by the probe mark,
    highlighting, by a controller of the ultrasound diagnostic apparatus, the second body mark corresponding to an examination being currently executed, and
    displaying a body mark corresponding to the highlighted second body mark together with die ultrasound image corresponding to the examination being currently executed on a second display screen different from the first display screen.

2. The method according to claim 1,
    wherein in execution of the series of examinations, after an examination of an examination portion which is executed by freezing an ultrasound image is finished, the highlighting switches highlighting of a second body mark corresponding the examination portion to another second body mark corresponding another examination portion which next undergoes an examination, when freezing of the ultrasound image is released.

3. The method according to claim 2,
    wherein in response to selecting one second body mark, the highlighting switches highlighting of the second body marks starting from the selected second body mark in an order of time series.

4. The method according to claim 3,
    wherein in response to selecting a later second body mark through the selecting while leaving second body marks of examination portions which have not yet undergone examinations, the controlling skips the second body marks of examination portions which have not yet undergone examinations and switches highlighting of second body marks starting from the selected later second body mark in an order of time series.

5. The method according to claim 3,
    wherein in response to selecting a second body mark of an examination portion which has already undergone an examination through the selecting, the highlighting switches highlighting of second body marks starting from the selected second body mark among the series of second body marks in an order of time series.

6. The method according to claim 1,
    wherein in execution of the series of examinations, after an examination of an examination portion which is executed by freezing an ultrasound image is finished, the highlighting switches highlighting of a second body mark corresponding the examination portion to another second body mark corresponding another examination portion which next undergoes an examination, when imaging mode is switched.

7. The method according to claim 6,
    wherein in response to selecting one second body mark, the highlighting switches highlighting of the second body marks starting from the selected second body mark in an order of time series.

8. The method according to claim 7,
    wherein in response to selecting a later second body mark through the selecting while leaving second body marks of examination portions which have not yet undergone examinations, the controlling skips the second body marks of examination portions which have not yet undergone examinations and switches highlighting of second body marks starting from the selected later second body mark in an order of time series.

9. The method according to claim 7,
    wherein in response to selecting a second body mark of an examination portion which has already undergone an examination through the selecting, the highlighting switches highlighting of second body marks starting from the selected second body mark among the series of second body marks in an order of time series.

10. The method according to claim 1,
    wherein in response to selecting one second body mark, the highlighting switches highlighting of second body marks starting from the selected second body mark in an order of time series.

11. The method according to claim 10,
    wherein in response to selecting a later second body mark through the selecting while leaving second body marks of examination portions which have not yet undergone examinations, the controlling skips the second body marks of examination portions which have not yet undergone examinations and switches highlighting of second body marks starting from the selected later second body mark in an order of time series.

12. The method according to claim 10,
wherein in response to selecting a second body mark of an examination portion which has already undergone an examination through the selecting, the highlighting switches highlighting of second body marks starting from the selected second body mark among the series of second body marks in an order of time series.

13. The method according to claim 10,
wherein in response to selecting a second body mark which is not included in the series of examinations through the selecting in the middle of the series of examinations, interrupting the series of examinations and the highlighting highlights the selected second body mark on the first display screen, and wherein when an examination corresponding to the selected second body mark is finished, the controlling returns to the series of examinations.

\* \* \* \* \*